(12) United States Patent
Wyart et al.

(10) Patent No.: US 10,113,053 B2
(45) Date of Patent: Oct. 30, 2018

(54) ISOSORBIDE EPOXIDE DIESTERS, AND THE USE THEREOF AS A PLASTICIZER IN PVC COMPOSITIONS

(71) Applicant: Roquette Freres, Lestrem (FR)

(72) Inventors: Hervé Wyart, Cuinchy (FR); Clothilde Buffe, Lomme (FR); Juliette Brocard, Béthune (FR)

(73) Assignee: ROQUETTE FRERES, Lestrem (FR)

( * ) Notice: Subject to any disclaimer, the term of this patent is extended or adjusted under 35 U.S.C. 154(b) by 43 days.

(21) Appl. No.: 15/514,805

(22) PCT Filed: Sep. 22, 2015

(86) PCT No.: PCT/FR2015/052538
§ 371 (c)(1),
(2) Date: Mar. 27, 2017

(87) PCT Pub. No.: WO2016/046490
PCT Pub. Date: Mar. 31, 2016

(65) Prior Publication Data
US 2017/0321036 A1      Nov. 9, 2017

(30) Foreign Application Priority Data

Sep. 23, 2014   (FR) ...................................... 14 58962

(51) Int. Cl.
*C07D 493/04*      (2006.01)
*C08L 27/06*       (2006.01)
*C08K 5/1535*      (2006.01)

(52) U.S. Cl.
CPC .......... *C08K 5/1535* (2013.01); *C07D 493/04* (2013.01)

(58) Field of Classification Search
CPC ........................... C08K 5/1535; C07D 494/04

USPC .......................................................... 524/109
See application file for complete search history.

(56) References Cited

U.S. PATENT DOCUMENTS

| | | | |
|---|---|---|---|
| 2,387,842 A | 10/1945 | Soltzberg et al. | |
| 3,225,067 A | 12/1965 | Maistre et al. | |
| 6,395,810 B1 * | 5/2002 | Luitjes | C07D 493/04 523/218 |
| 8,258,325 B2 | 9/2012 | Grass et al. | |
| 8,609,872 B2 | 12/2013 | Fuertes et al. | |
| 9,505,909 B2 | 11/2016 | Grass et al. | |
| 2006/0020062 A1 * | 1/2006 | Bloom | C07D 303/42 524/114 |
| 2015/0322238 A1 | 11/2015 | Feron et al. | |

FOREIGN PATENT DOCUMENTS

| | | |
|---|---|---|
| WO | WO 9945060 A1 | 9/1999 |
| WO | WO 2006/103338 A1 | 10/2006 |
| WO | WO 2008/095571 A1 | 8/2008 |
| WO | WO 2013/092655 A1 | 6/2013 |
| WO | WO 2014/080151 A1 | 5/2014 |
| WO | WO 2014/080152 A1 | 5/2014 |

OTHER PUBLICATIONS

Y. Hachihama et al., "Studies on the Preparation of Plasticizers from Carbohydrate Sources." Technology Reports of the Osaka University, vol. 3, No. 72, pp. 191-200, 1953.

* cited by examiner

*Primary Examiner* — Kelechi C Egwim
(74) *Attorney, Agent, or Firm* — Oliff PLC

(57) ABSTRACT

The invention relates to isosorbide epoxide esters having Formulas (I), (II), and (III), to the mixtures thereof, and to the use thereof as an additive in PVC compositions, particularly as a plasticizer.

20 Claims, No Drawings

ISOSORBIDE EPOXIDE DIESTERS, AND THE USE THEREOF AS A PLASTICIZER IN PVC COMPOSITIONS

This application is a national stage of International Patent Application No. PCT/FR2015/052538, filed Sep. 22, 2015, which claims the benefit of French Patent Application 1458962, filed Sep. 23, 2014, each of which is hereby incorporated by reference in its entirety.

The invention relates generally to epoxidized esters of isosorbide, and the use thereof as additive in PVC formulations, especially as plasticizer.

Polyvinyl chloride is a mass-produced thermoplastic polymer, which is amorphous or slightly crystalline, known under the acronym PVC for PolyVinyl Chloride. It is generally formulated with additives such as stabilizers, fillers, pigments and plasticizers, and is currently widespread in numerous applications.

PVC is a rigid material which may be used to manufacture pipes, with these representing more than 40% of the global consumption of PVC. It is also possible to add plasticizers thereto, the role of which is to improve the flexibility thereof, but also the elongation at break thereof, the resistance thereof to cold and impacts, and more generally the workability thereof. It may then be in "expanded" form (often referred to as FOREX), used especially for producing advertising billboards, or in the form of plasticized films serving as adhesives or packaging materials, and finally in the form of flexible PVC proper, mainly in floor and ceiling covering applications.

Most plasticizers used in PVCs are organic liquids which are non-volatile or which have a low melting point, the mechanism of action of which relies on a reduction of the intermolecular forces in the PVC resin, thereby enabling the macromolecules of vinyl chloride to "slide" more freely over one another. By increasing the "free volume" between the polymer chains, they lower the glass transition temperature of the PVC, which contributes to making the latter more flexible.

These plasticizers are based on esters of polycarboxylic acids with linear or branched aliphatic alcohols. The most well-known for PVC are phthalates, compounds based on adipate and trimellitate. By way of examples of plasticizers based on phthalate, mention may be made of diisononyl phthalate (DINP), di-2-ethylhexyl phthalate (DEHP), dibutyl phthalate (DBP), diisodecyl phthalate (DIDP), or dibenzylbutyl phthalate (BBP).

Phthalates are organic pollutants that are very widespread in the environment of urban areas. The labelling of these compounds requires the statement "toxic" and some also carry the statement "hazardous to the environment". The use of some phthalates in childcare articles or toys intended for children under 3 years of age has especially been banned for some years and is frequently revised (see European Union directive 2005/84/CE [PDF] and the decree no. 2006-1361 of Nov. 9, 2006, transposing the Directive into French law).

For the other plastics materials, no regulations are in force since the doses at which these plasticizers are used are not considered to be dangerous. The fact still remains that the most widespread phthalates (DEHP, DBP, DINP, DIDP and BBP) are still the subject of numerous studies by various international bodies (Food and Drug Administration, European Chemicals Bureau and the Institut National de Santé Publique au Québec [National Institute for Public Health in Quebec]).

Thus, there is a constant need to find novel plasticizers for thermoplastic materials and especially PVC, which have plasticizing properties at least equivalent to those of the phthalates while favoring a bio-based origin.

To this end, 1,4:3,6-dianhydrohexitols, and more particularly esters of 1,4:3,6-dianhydrohexitols, and even more preferably fatty acid esters of the particular compound isosorbide form a promising lead.

As regards 1,4:3,6-dianhydrohexitols, these compounds, also referred to as isohexides, are obtained by the internal dehydration of hydrogenated $C_6$ sugars (hexitols) such as sorbitol, mannitol and iditol. In the present application, the term "1,4:3,6-dianhydrohexitols" encompasses isosorbide (1,4:3,6-dianhydrosorbitol), isomannide (1,4:3,6 dianhydromannitol) and isoidide (1,4:3,6-dianhydroiditol) of the following formulae, and also the mixtures of these products:

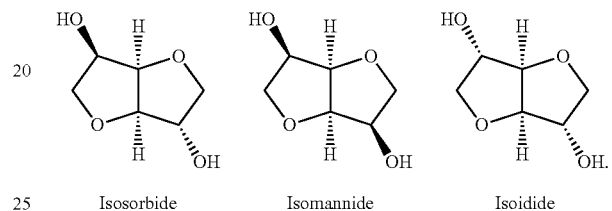

Isosorbide    Isomannide    Isoidide

As regards the fatty acids or plant oils, it is recalled that these products denote aliphatic-chain carboxylic acids. Natural fatty acids have a carbon-based chain with 4 to 36, and typically an even number, of carbon atoms. Fatty acids are present in animal fats and plant fats, plant oils or waxes, in the form of esters.

The use of 1,4:3,6-dianhydrohexitol derivatives as polymer plasticizers has already been described in document WO 99/45060. The examples from this application describe plasticizers that are liquid at room temperature: isosorbide dioctanoate, isosorbide dibutanoate, isosorbide dihexanoate and isosorbide di(2-ethylhexanoate). These plasticizers are also described in document WO 2008/095571 A1, which describes aliphatic diesters containing 9 carbon atoms. The document "Preparation of plasticizers from carbohydrate sources. I. Levulinic acid esters. II. Sorbide esters", (Hachihama et al., Technology reports of the Osaka University, Vol. 3, no. 72, 1953, pages 191-200) describes aliphatic esters containing 8 carbon atoms and also aliphatic esters containing 10 carbon atoms. U.S. Pat. No. 2,387,842 describes mixed aliphatic diesters, these also being useful as plasticizers. Mixtures of this type of esters are also described in applications WO 2014/080151 A1 and WO 2014/080152 A1, such products being able to be obtained from 1,4:3,6 dianhydrohexitols and mixtures of fatty acids.

Thus, there is a constant need to develop novel products based on esters of 1,4:3,6-dianhydrohexitols that are able to be made use of as plasticizers in PVC-based compositions. In this context, the applicant company has succeeded in synthesizing such molecules. The latter consist of epoxidized diesters of isosorbide fatty acids, more precisely of epoxidized diesters of isosorbide oleic, linoleic and linolenic acids, and also the mixtures thereof, the individual compounds being those given by the following formulae (I), (II) and (III):

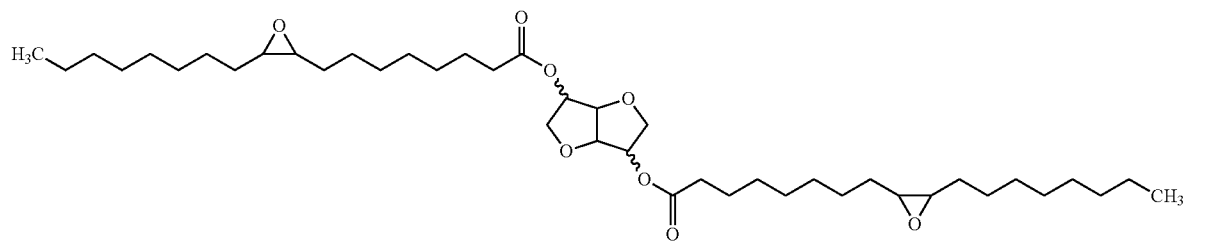

(I)

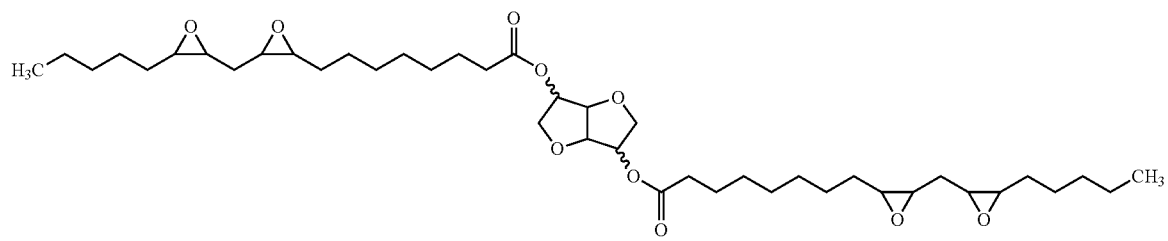

(II)

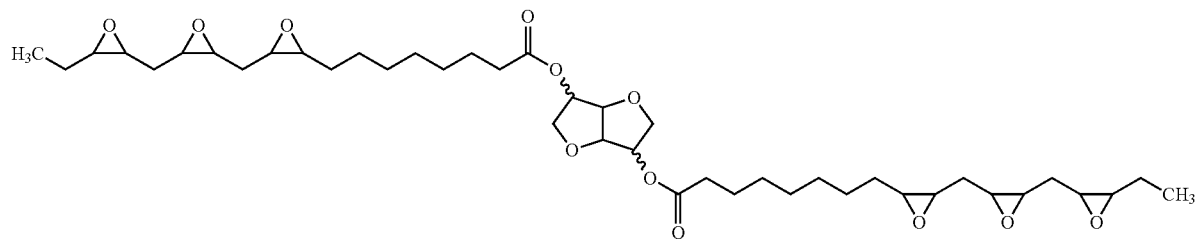

(III)

The applicant company notes that epoxidized esters of 1,4:3,6-dianhydrohexitol fatty acids are moreover already known. Thus, document U.S. Pat. No. 3,225,067 describes epoxidized diesters of polyoxyethylene isosorbide containing from 2 to 8 oxyethylene groups per mole and 2 mol of ethylenic unsaturated fatty acids with a degree of epoxidation of at least 25% of the unsaturated groups.

Document WO 2013/092655 is also known, which describes a mixture of esters of dianhydrohexitol, said mixture having an average chain length of between 8.3 and 9.2, said esters moreover possibly being epoxidized.

Finally, document US 2006 020062 is known, which describes epoxidized esters of fatty acids and of plant oils which may, in some cases, be epoxidized esters of isosorbide. These products may be used as plasticizer in PVC-based compositions.

This being said, and to the best of the applicant's knowledge, none of these documents, nor any other document from the prior art, describes or discloses any one of the three abovementioned compounds represented through the formulae (I), (II) and (III). In addition, and both surprisingly and advantageously, the compounds which are the subject of the present application prove to be highly compatible with PVC and have a very good aptitude for plasticizing it, unlike their non-epoxidized homologs (e.g. the esters of 1,4:3,6-dianhydrohexitols which have not been subjected to the epoxidation reaction according to the present invention).

In the case of the present application, the compatibility of the compound with PVC is characterized by the dry-blending time measured during the step of dry mixing, which is the time from the introduction of the compound into the PVC resin until the complete absorption thereof by the PVC resin. A low compatibility of a plasticizer with the PVC may lead to a loss of flexibility of the PVC plate over time, to the appearance of opaqueness (in the case of a formula without filler and without pigment) and/or a greasy feel on the surface. In addition, a high dry-blending time may, depending on the PVC transformer process, risk slowing down the process for manufacturing plasticized PVC and thus lead to a loss of productivity.

The ability of the compound to plasticize PVC is, for its part, characterized in that the PVC plate obtained after the transformation process is cohesive, flexible and strong all at the same time.

Thus, a first subject of the present invention relates to the abovementioned epoxidized diesters of isosorbide of formulae (I), (II) and (III).

Another subject of the present invention relates to all the mixtures of these different products, that is to say the mixture of two or three compounds from the compounds of formula (I), formula (II) and formula (III).

These mixtures may typically have an iodine index of less than 10 g $I_2$/100 g, preferentially less than 6 g $I_2$/100 g and an oxirane content of greater than 3%.

The iodine index is measure according to the standard NF/EN/ISO 3961 (Sep. 14 2013). It is expressed in g of iodine per 100 g of product.

The % of oxirane is defined as the % by weight of oxygen relative to the total weight of the product and is determined by NMR.

Another subject of the present invention relates to the use of these products or the mixtures thereof as plasticizer in PVC-based compositions.

The compounds of formulae (I), (II) and (III) and the mixtures thereof are moreover able to be obtained by known processes.

The first step of such a process consists in a reaction for esterification of the isosorbide. This step may be carried out by any known method for esterification of 1,4:3,6-dianhydrohexitol and especially isosorbide by a carboxylic acid, said process being characterized in that one of oleic, linoleic and linolenic acids, or one of the mixtures thereof, is used instead of the acid. These acids may especially be the products sold by OLEON under the names Nouracid 1880, Nouracid HE 30 and Nouracid LE 80.

Esterification methods are described for example in documents WO 99/45060 A1 and WO 2006/103338 A1.

It is possible to carry out the esterification step in the presence of at least one acid catalyst. The latter may be of very varied nature: it may be an acid chosen from hypophosphorous acid, hydrochloric acid, sulfuric acid, para-toluenesulfonic acid (PTSA), methanesulfonic acid (MSA), trifluoromethanesulfonic acid, trifluoroacetic acid, trichloroacetic acid, tin 2-ethylhexanoate, phosphotungstic acid and silicotungstic acid or a mixture of these acids or a macroporous or non-macroporous resin comprising at least one of these acids. Preferably, the catalyst comprises hypophosphorous acid. In the case of mixtures of catalysts, they may be introduced into the reaction medium simultaneously or separately.

The % by weight of acid catalyst may range from 0.05% to 20%, for example from 0.1% to 10%, relative to the weight of isosorbide introduced into the reactor. The temperature in the reactor may range from 90 to 200° C., generally from 100 to 150° C. To perform the esterification reaction, the water is generally eliminated so as to allow the formation of the diester, this elimination possibly being carried out, for example, by distillation of the reaction medium. In order to facilitate this elimination, the reaction medium may be placed under vacuum, for example under a vacuum corresponding to a negative pressure of between 10 and 200 mbar. The reaction conditions such as the level of vacuum and the temperature during the reaction may be varied.

The esterification reaction is generally continued until a satisfactory degree of conversion into isosorbide diester of at least 90% is obtained. It may last from 1 to 10 hours.

A step of neutralizing the catalyst may also be carried out, by introducing a base, for example sodium hydroxide, in molar amounts equivalent to the molar amounts of catalyst introduced.

The manufacturing process may also comprise a subsequent step of purifying the diester composition. This advantageously consists of at least one evaporation step, for example by distillation, making it possible to remove the majority or virtually all of the acid still present after the esterification step. During this step, the diester composition may be subjected to a temperature of between 100 and 250° C. and to a negative pressure of between 0.1 and 50 mbar. Preferably, this step takes place in a continuous evaporator. Such an evaporator, for example of "falling film" type or, better still, of scraped film or "short path" type, makes it possible to limit the temperatures and residence times to which the composition is subjected after the esterification step.

The process may also comprise a step of decolorizing the diester composition, for example by using active charcoals or hydrogen peroxide. The treatment with active charcoal takes place, for example, by placing the composition in contact with 1% to 3% by weight of active charcoal. The temperature during this treatment may be in the region of 100° C. The duration is generally between 10 minutes and 1 hour. At the end of the treatment, the active charcoal is eliminated by filtration. A standard decolorizing treatment with hydrogen peroxide consists, for example, in introducing into the composition to be decolorized, over a period ranging, for example, from 30 to 60 minutes, from 0.5% to 2% of 100% hydrogen peroxide, at a temperature of between 90° C. and 150° C., then stirring the composition for 1 to 2 hours at this temperature. When it is desired to combine these two types of decolorizing treatment, the hydrogen peroxide treatment preferably precedes that with active charcoal. This is because the active charcoal makes it possible to destroy the peroxides that may be present.

The second step of the process consists of the epoxidation of the isosorbide diester composition obtained previously. This step may be carried out according to any known processes for epoxidation of isosorbide diester. Document US 2006 020062, already cited in the present application, is an illustration thereof.

The epoxidation reaction consists in placing the diester composition obtained previously in the presence of at least one agent containing the peroxide function. This agent may especially be chosen from hydrogen peroxide, peroxycarboxylic acids or alkyl hydroperoxides. Preference will be given to hydrogen peroxide.

In the presence of hydrogen peroxide, an acid is added, especially formic acid or acetic acid, in order to form the most reactive corresponding peracid in situ.

The reaction may be catalysed in the presence of another acid such as sulfuric acid or a strong cationic resin especially the resin sold by Dow under the name Amberlyst 15.

The choice may be made to add surfactants to facilitate the dispersion of the oil phase within the aqueous phase.

The progression of the reaction may be monitored by the disappearance of the NMR signal between 2.8 and 3.2 ppm, corresponding to the ethylene protons.

The reaction is carried out at between 20 and 60° C., preferentially between 30 and 50° C., at atmospheric pressure.

At the end of the reaction, in order to facilitate the washing operations, the organic phase may be diluted in a water-immiscible organic solvent, such as ethyl acetate. The presence of residual peroxide is eliminated by washing by means of a solution of sodium bisulfite. The acetic or formic acid is eliminated by washing with water.

The product is recovered after evaporation of the organic solvent under reduced pressure on a rotavap.

Another subject of the present invention relates to the use of the abovementioned products or the mixtures thereof as plasticizer in PVC formulations.

Another subject of the present invention relates to a PVC formulation comprising polyvinyl chloride and one of the compounds of formula (I), (II) or (III) according to the invention, or one of the mixtures thereof.

Another subject of the present invention relates to a finished or semi-finished plastic article comprising polyvinyl chloride and one of the compounds of formula (I), (II) or (III) according to the invention, or one of the mixtures thereof.

"PVC formulation" is intended to mean, in the present description, thermoplastic formulations, the predominant polymer component of which is PVC (typically a polymer composition containing at least 80% by weight of PVC).

Aside from the compounds according to the present invention, said PVC formulation may contain other conventional additives such as mineral or organic fillers, stabilizers, pigments, flame retardants or lubricants. It may be in the form of a dry blend, granules or plastisols.

Once the compounds which are the subject of the present invention have been synthesized, they may then be used in PVC formulations. They are conventionally mixed with PVC according to different processes. The PVC may then be transformed into an object via various techniques for transforming thermoplastic materials, and in particular by extrusion, by calendering or else by coating via a process of plastisol type.

In order to obtain this thermoplastic mixture, the PVC is mixed with the plasticizer while supplying energy to this system, in the form of temperature and mechanical energy. In the case of extrusion, this mixing takes place in a closed system. In the case of mixing on rolls, this mixing takes place in an open system. The polymer may then be formed, for example via thermoforming or calendering processes. Generally, a step of dry blending is performed before the thermomechanical mixing step. According to the plastisol process, mixing is generally carried out to form a PVC paste, this paste is then formed via a coating or molding step, and the paste is then heated in an oven to form the component.

The examples which follow make it possible to better understand the present invention, without however limiting the scope thereof.

EXAMPLES

Analytical Methods

In all the following examples, the analytical methods used are as follows.

The amount by weight of diester obtained after the esterification reaction is measured by gas chromatography. The column used is a 30 meter long ZB1HT with an internal diameter of 0.32 mm and a film thickness of 0.25 μm. The amount by weight of diester is given by the ratio of the sum of the areas of the compounds corresponding to the isosorbide diesters to the sum of the areas of all the compounds.

The degree of unsaturation of the fatty chain of the isosorbide diester is determined by measuring the iodine index according to standard NF/EN/ISO 3961 (Sep. 14 2013). It is expressed in g of iodine per 100 g of product.

The % of oxirane is defined as the % by weight of oxygen relative to the total weight of the product and is determined by NMR.

Example 1

This example relates to the synthesis of isosorbide diesters from isosorbide and different commercial fatty acids which are fractions of oleic, linoleic and linolenic acids.

Test No. 1

146 g of isosorbide (1 mol) and 564 g (2 mol) of Nouracid 1880 (oleic acid-rich fatty acid), provided by OLEON, containing 79.3% by weight of oleic acid (C18:1), 12.1% of linoleic acid (C18:2) and 0.1% of linolenic acid (C18:3), are introduced into a 1 liter glass reactor fitted with a jacket supplied by a thermostatic circulating oil bath, a stirrer blade, a thermometer and a distillation head combined with a condenser and a distillation receiver.

The stirring system is switched on at 400 rpm, and the thermostatic bath is switched on at a nominal temperature of 100° C. When the temperature of the reaction medium reaches 60° C., 2.92 g of p-toluenesulfonic acid (PTSA) monohydrate (2% commercial relative to the dry isosorbide) and 0.90 g of 50% hypophosphorous acid, i.e. 0.3% of dry matter relative to the dry isosorbide, are added. The nominal temperature of the thermostatic bath is then set at 160° C. and the stirring is set at 650 rpm. The mounting assembly is then connected to a vacuum pump equipped with a vacuum gauge, the nominal pressure of which is set at 100 mbar.

When the temperature of the reaction medium reaches approximately 115° C., the water derived from the esterification reaction is distilled off and collected in the receiver. The vacuum is then gradually lowered over 4 hours to 30 mbar, and the nominal temperature of the thermostatic bath increased by 10° C. per hour, to reach 200° C. After 4 hours, the temperature of the reaction medium is 185° C. The nominal temperature of the thermostatic bath is then fixed at 220° C. and the reaction is continued for 2 hours. After 6 hours of reaction, the temperature of the reaction medium is 210° C. The reaction medium is then cooled to approximately 100° C., and the PTSA and hypophosphorous acid strong acidities are neutralized by adding 1.8 g of 50% sodium hydroxide.

The unreacted fatty acid is then distilled off under vacuum (pressure: <2 mbar) with a jacket temperature of 250° C. After cooling to 100° C., the product is decolorized by treatment with active charcoal. The composition thus purified has an amount by weight of isosorbide diester of 99.0% and an iodine index of 79 g $I_2$ per 100 g of product.

Test No. 2

This test is carried out according to the operating protocol of the previous test, substituting the oleic acid-rich fatty acid with Nouracid HE30 (OLEON), a linoleic acid-rich fatty acid containing 29.2% by weight of oleic acid (C18:1), 58.3% of linoleic acid (C18:2) and 0.4% of linolenic acid (C18:3).

The final composition obtained has an amount by weight of isosorbide diesters of 97.7% and an iodine index of 110.9 g $I_2$ per 100 g of product.

Test No. 3

A test 3 is carried out according to the operating protocol of test no. 1, substituting the oleic acid-rich fatty acid with Nouracid LE80 (OLEON), a linolenic acid-rich fatty acid containing 20.3% by weight of oleic acid (C18:1), 18% of linoleic acid (C18:2) and 50.1% of linolenic acid (C18:3).

The final composition obtained has an amount by weight of isosorbide diesters of 97.2% and an iodine index of 151 g $I_2$ per 100 g of product.

Example 2

This example relates to the reaction for epoxidation of the esters obtained during the previous example. The products according to the present invention are obtained here.

Test No. 4

100 g of the compound obtained in test no. 1 (0.31 mol of unsaturations), 352.5 g of a 30% aqueous solution of hydrogen peroxide (3.1 mol), 35.8 g of formic acid (0.78 mol) and 0.2 g of Tween 20 (0.2% by weight relative to the diester) are introduced into a 1 liter glass reactor fitted with a jacket supplied by a thermostatic circulating water bath, a stirrer blade, a thermometer and a condenser.

The stirring system is switched on at 200 rpm, and the thermostatic bath is switched on at a nominal temperature of 30° C. After 24 h of reaction, the reaction medium is extracted with ethyl acetate. The organic phase is washed using an aqueous solution of sodium bisulfite then with water. The organic phase is dried with anhydrous magnesium sulfate, filtered and concentrated on a rotavap.

The finished product has an iodine index of 1.6 g $I_2$/100 g of crude. NMR analysis confirms the presence of epoxide units (signal between 2.8 and 3.2 ppm). The oxirane content is 3%.

Test No. 5

200 g of the compound obtained in test no. 2 (0.87 mol of unsaturations), 148.6 g of a 30% aqueous solution of hydrogen peroxide (1.3 mol), 20.1 g of formic acid (0.44 mol) and 20 g of Amberlyst 15 (10% by weight relative to the diester) are introduced into a 1 liter glass reactor fitted with a jacket supplied by a thermostatic circulating water bath, a stirrer blade, a thermometer and a condenser.

The stirring system is switched on at 200 rpm, and the thermostatic bath is switched on at a nominal temperature of 30° C. After 24 h of reaction, the reaction medium is extracted with ethyl acetate. The organic phase is washed using an aqueous solution of sodium bisulfite then with water. The organic phase is dried with anhydrous magnesium sulfate, filtered and concentrated on a rotavap.

The finished product has an iodine index of 0.6 g $I_2$/100 g of crude. NMR analysis confirms the presence of epoxide units (signal between 2.8 and 3.2 ppm). The oxirane content is 3.4%.

Test No. 6

This test is carried out according to the operating protocol of the previous test but starting from the product obtained according to test no. 3.

The finished product has an iodine index of 3.6 g $I_2$/100 g of crude. NMR analysis confirms the presence of epoxide units (signal between 2.8 and 3.2 ppm). The oxirane content is 5.2%.

Example 3

This example describes the use as plasticizer, in a PVC formulation:
- of the 3 non-epoxidized esters of isosorbide obtained according to tests nos. 1 to 3
- of the 3 epoxidized esters of isosorbide obtained according to tests nos. 4 to 6

The plasticized PVC formulation according to the invention is composed of the following products:
MARVYLAN® S7102 PVC: 100 parts
BAEROSTAB® NT 319P stabilizer (Ca/Zn powder): 1.5 part
LANKROFLEX® E 2307 co-stabilizer (epoxidized soybean oil): 2 parts
Plasticizer: 34 parts The PVC plates are prepared in several steps:

1) Preparation of a dry blend of plasticized PVC:

A mass of 500 g of PVC (powder) is introduced into a Planetmix 500 type planetary mixer (from Thermo Scientific) equipped with a temperature regulation circuit, with the corresponding amount of thermal stabilizer and of thermal co-stabilizer. When the temperature of the mixture reaches 85° C., the plasticizer is poured over the entire surface of the PVC powder. The preparation is then mixed for a further 8 minutes after total absorption of the plasticizer into the PVC.

During this dry blending step, the measurement of the dry-blending time characterizes the rate of absorption of the plasticizer into the PVC and is obtained as follows. The Planetmix mixer used makes it possible to monitor the change in its motor torque throughout the mixing step. As soon as the plasticizer is introduced into the PVC, the torque increases as the plasticizer is added, until it reaches a maximum when all the plasticizer has been poured in. The torque then begins to decrease as the plasticizer is absorbed by the PVC. When it has been entirely absorbed, the torque measured reaches a minimum. The dry-blending time is thus defined as the time taken for the mixture, from the introduction of the plasticizer, to reach this minimum torque, and thus characterizes the rate of absorption of the plasticizer, linked to its compatibility with the PVC.

2) Preparation of plates of plasticized PVC:

Plates of plasticized PVC are formed using a Carver type press and a mirror-polished stainless steel 30×30 cm mold equipped with a frame 2 mm thick and a mirror-polished stainless steel lid. An amount of 180 g of plasticized PVC powder prepared in step 1) is uniformly poured into the frame placed inside the mold, and everything is then covered with a lid. The assembly is placed on the plateau of the press preheated to 185° C. and the program which consists in applying a closing force of 18 000 kg at 185° C. for 2 minutes is started. After cooling to a temperature close to 45° C., the PVC plate thus obtained is then removed from the mold.

The table below gives the dry-blending time values obtained during the dry blending step with the compounds of examples 1 to 6, and also the appearance of the plate of plasticized PVC on leaving the press.

| | Dry-blending time (s) | Appearance of the plate of plasticized PVC |
|---|---|---|
| Example 1 | 1474 - 1218 - 1380 | Non-cohesive, brittle, opaque, greasy |
| Example 2 | 1343 - 1402 - 1261 | Non-cohesive, brittle, opaque, greasy |
| Example 3 | 1352 - 1247 - 1499 | Non-cohesive, brittle, opaque, greasy |
| Example 4 | 466 - 403 - 451 | Cohesive, transparent and flexible |
| Example 5 | 442 - 516 - 464 | Cohesive, transparent and flexible |
| Example 6 | 529 - 493 - 458 | Cohesive, transparent and flexible |

This table shows that the compounds of examples 4 to 6 according to the invention are much more compatible with the PVC than the compounds of examples 1 to 3 outside the invention. Very advantageously, the compounds of examples 4 to 6 have a very good ability to plasticize the PVC by enabling the production of plates of flexible PVC with a flexible and transparent appearance, while examples 1 to 3 outside the invention do not make this possible.

The invention claimed is:

1. A compound of the following formula (I):

(I)

2. A polyvinyl chloride formulation comprising polyvinyl chloride and a compound of formula (I) as claimed in claim 1.

3. A plastic article comprising polyvinyl chloride and a compound of formula (I) as claimed in claim 1.

4. Plasticizer for a polyvinyl chloride formulation comprising a compound of formula (I) as claimed in claim 1 as plasticizer in a polyvinyl chloride formulation.

5. A process for preparing a polyvinyl chloride formulation comprising the mixing of a polyvinyl chloride with a compound of formula (I) as claimed in claim 1.

6. A compound of the following formula (II):

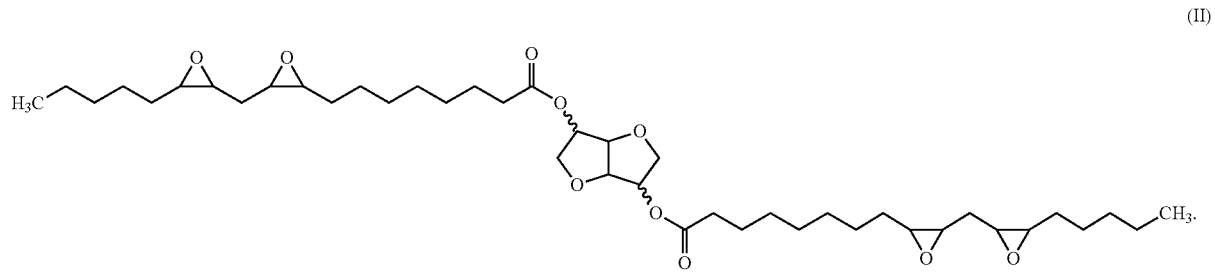 [SMILES: CCCCCC1OC1CC1OC1CCCCCCCC(=O)OC1COC2C(OC(=O)CCCCCCCC3OC3CC3OC3CCCCC)COC12]

(II)

7. A polyvinyl chloride formulation comprising polyvinyl chloride and a compound of formula (II) as claimed in claim 6.

8. A plastic article comprising polyvinyl chloride and a compound of formula (II) as claimed in claim 6.

9. Plasticizer for a polyvinyl chloride formulation comprising a compound of formula (II) as claimed in claim 6.

10. A process for preparing a polyvinyl chloride formulation comprising the mixing of a polyvinyl chloride with a compound of formula (II) as claimed in claim 6.

11. A compound of the following formula (III):

13. A plastic article comprising polyvinyl chloride and a compound of formula (III) as claimed in claim 11.

14. Plasticizer for a polyvinyl chloride formulation comprising a compound of formula (III) as claimed in claim 11.

15. A process for preparing a polyvinyl chloride formulation comprising the mixing of a polyvinyl chloride with a compound of formula (III) as claimed in claim 11.

16. Mixtures of compounds of formulae (I), (II) and (III):

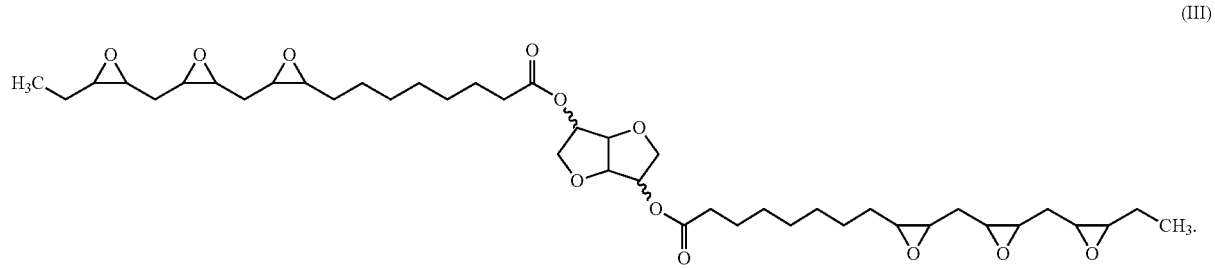 [SMILES: CCC1OC1CC1OC1CC1OC1CCCCCCCC(=O)OC1COC2C(OC(=O)CCCCCCCC3OC3CC3OC3CC3OC3CC)COC12]

(III)

12. A polyvinyl chloride formulation comprising polyvinyl chloride and a compound of formula (III) as claimed in claim 11.

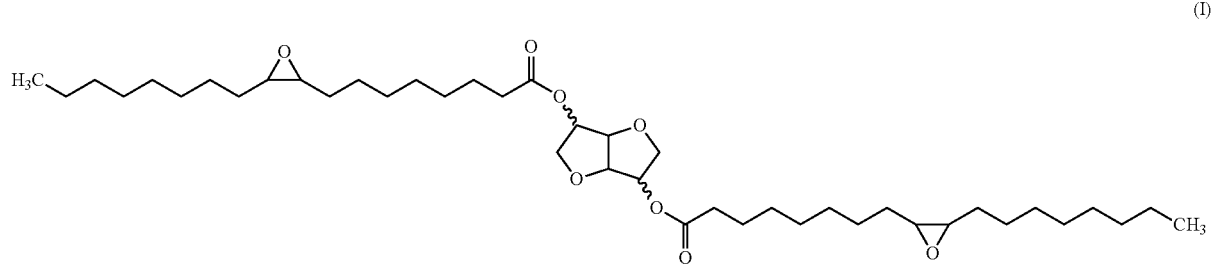

(I)

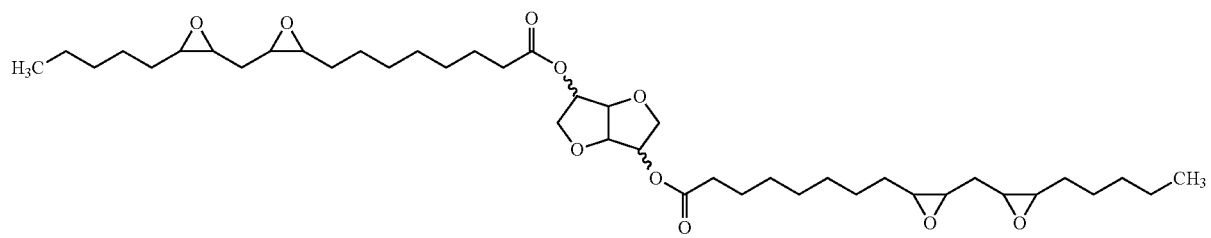

(II)

-continued

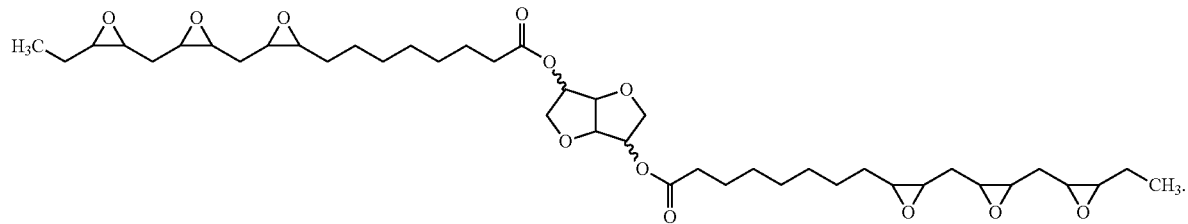

(III)

17. A polyvinyl chloride formulation comprising polyvinyl chloride and a mixture of compounds of formulae (I), (II) and (III) as claimed in claim 16.

18. A plastic article comprising polyvinyl chloride and a mixture of compounds of formulae (I), (II) and (III) as claimed in claim 16.

19. Plasticizer for a polyvinyl chloride formulation comprising a mixture of compounds of formulae (I), (II) and (III) as claimed in claim 16.

20. A process for preparing a polyvinyl chloride formulation comprising the mixing of a polyvinyl chloride with a mixture of compounds of formulae (I), (II) and (III) as claimed in claim 16.

* * * * *